United States Patent [19]

Alderman

[11] Patent Number: 4,873,432
[45] Date of Patent: Oct. 10, 1989

[54] COMPOUND APPLICATION DETECTOR

[75] Inventor: George W. Alderman, Barrington, Ill.

[73] Assignee: American National Can Company, Chicago, Ill.

[21] Appl. No.: 236,640

[22] Filed: Aug. 25, 1988

[51] Int. Cl.[4] .......................... H01J 5/16; B65B 7/00
[52] U.S. Cl. ..................................... 250/227; 156/69; 156/356; 156/578
[58] Field of Search .................... 250/227; 156/59, 64, 156/69, 356, 578

[56] References Cited

U.S. PATENT DOCUMENTS

| | | | |
|---|---|---|---|
| 4,046,306 | 9/1977 | Cass | 156/69 |
| 4,297,161 | 10/1981 | Graffin | 156/69 |
| 4,484,964 | 11/1984 | Kawamata | 156/69 |
| 4,569,717 | 2/1986 | Ohgami et al. | 250/227 |

Primary Examiner—David C. Nelms
Assistant Examiner—Stephone B. Allen
Attorney, Agent, or Firm—Wallenstein, Wagner & Hattis, Ltd.

[57] ABSTRACT

A detector for a can making apparatus applying a compound to a seaming flange of a can end, the detector for detecting the presence of said compound on said seaming flange of said can end.

13 Claims, 1 Drawing Sheet

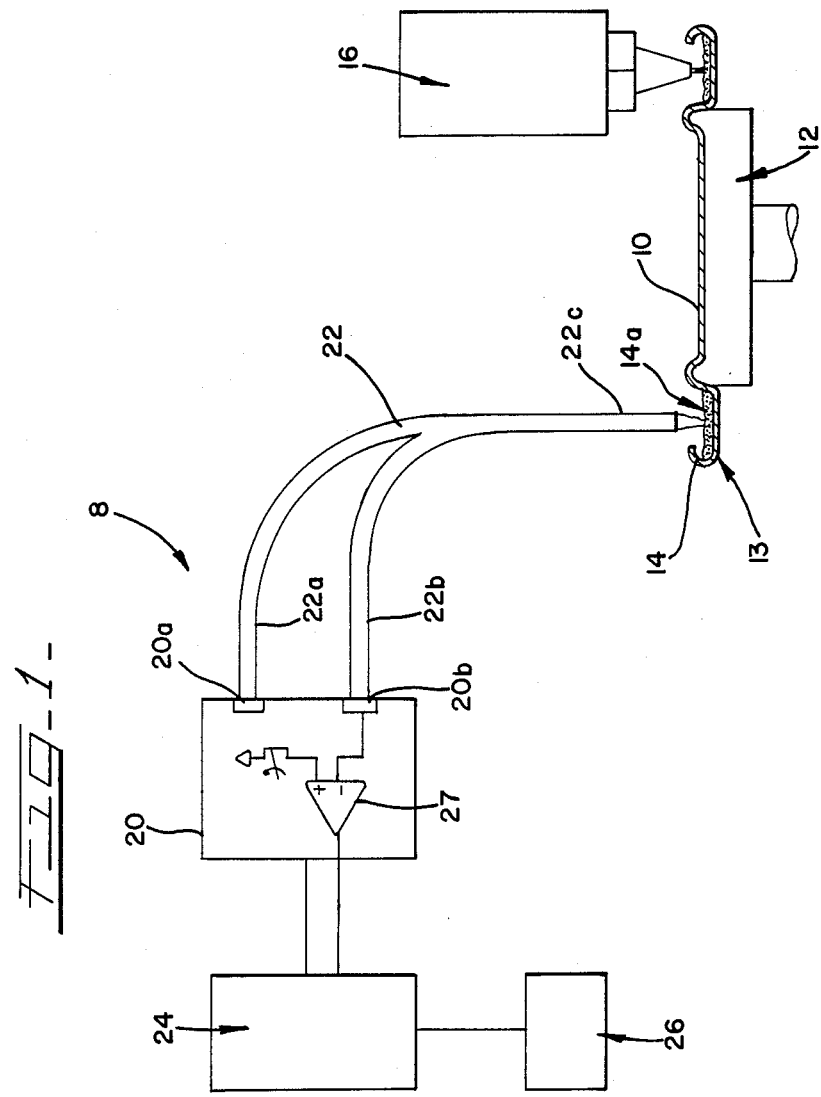

COMPOUND APPLICATION DETECTOR

DESCRIPTION

1. Technical Field

This invention relates to an apparatus for producing a can and, more particularly, to an apparatus for detecting whether compound has been applied to a seaming flange of a can end prior to joining the end to a can body.

2. Background Prior Art

Typically a can is produced by joining a can end, commonly referred to in the industry simply as an "end", to a can body. Such cans can be either a two piece can or a three piece can. Specifically two piece cans are produced by joining a single can end to a cylindrical can body having a bottom formed integrally with the can body. Three piece cans are produced by joining two can ends to a cylindrical can body having opposing openings. In either case, the can end or ends to be joined includes seaming flanges which mechanically cooperate with respective seaming flanges on the can body to provide a mechanical joint.

Before joining the can end to the can body, a compound is preferrably applied to the well of the seaming flange of the can end to act as a sealant or gasket. Because of production demands, the compound is applied by compound applying machinery to the can ends at a rate of the order of 800 can ends per minute. At this production rate, visual inspection to determine proper application of the compound to each and every can end is difficult if not impossible.

Prior art detectors have utilized infrared sensors in combination with complex focusing lenses in an attempt to detect the proper application of the compound. Because these detectors were bulky and had to be mounted in close proximity to the rapidly moving can ends, they were extremely difficult to incorporate into the compound applying machinery. In addition, the requirement for accurate lenses made these prior art detectors expensive.

SUMMARY OF THE INVENTION

It is an object of the present invention to provide a detector for a can making apparatus for detecting proper application of a sealing compound to a seaming flange of a can end.

In accordance with the present invention, the detector comprises means for generating an infrared signal, means for receiving an infrared signal and a first fiber optic cable having a first end coupled to the infrared signal generating means and a second end directed toward the seaming flange of the can end. The first fiber optic cable transmits the generated infrared signal toward the seaming flange, causing it to reflect a portion of the generated signal as a reflected signal. The seaming flange reflects a first proportion of the generated infrared light in the absence of the compound and a second proportion of the generated infrared light in the presence of the compound. The detector further includes a second fiber optic cable having a first end directed toward the seaming flange and a second end coupled to the infrared signal receiving means. The second fiber optic cable transmits the reflected infrared signal from the seaming flange to the infrared signal receiving means. In addition, the detector includes means for comparing the reflected infrared signal received by the infrared signal receiving means to a reference value representing a desired thickness of the compound applied to the seaming flange and means for generating a reject signal in the event that the comparing means indicates that less than the desired thickness of the compound has been applied. It is comprehended that the reference value is adjustable to accommodate different compouns. The detector further includes means for rejecting the can end in response to the reject signal.

According to one aspect of the present invention, the first and second fiber optic cables together comprise a bifurcated fiber optic cable. Accordingly the bifurcated fiber optic cable has first and second split ends and a common end. The first split end is coupled to the infrared generating means, the second split end is coupled to the infrared receiving means, and the common end is directed toward the seaming flange.

It is still further comprehended that the second end of the first fiber optic cable and the first end of the second fiber optic cable are positioned a distance of the order of $\frac{1}{4}''$ to $\frac{3}{8}''$ away from the seaming flange.

Other features and advantages of the invention will be apparent from the following specification taken in conjunction with the following drawing.

BRIEF DESCRIPTION OF DRAWINGS

FIG. 1 is a block diagram of a detector according to the invention.

DETAILED DESCRIPTION

While this invention is susceptible of embodiments in many different forms, there is shown in the drawing and will herein be described in detail, a preferred embodiment of the invention with the understanding that the present disclosure is to be considered as an exemplification of the principles of the invention and is not intended to limit the broad aspects of the invention to the embodiment illustrated.

FIG. 1 illustrates a detector, generally designated 8, for detecting a presence of compound applied to a can end 10.

The can end 10 is shown mounted on a liner chuck 12 of a compound applying machine (not shown). The compound applying machine can be a Twin-Station Darex compound applying machine, distributed by the Dewey and Almy Chemical Division, W. R. Grace and Company, 55 Aden Avenue, Lexington, Mass. 02173.

The can end 10 includes a seaming flange 13 which mechanically cooperates with a respective seaming flange on a can body (not shown) to provide a double seam or mechanical joint between the can end 10 and a can body, as is well known in the art.

The seaming flange 13 includes a curl area 14 surrounding a well 14a. The compound applying machine applies a sealing compound to the wall 14a of the can end 10 via a compound gun 16 at a rate of approximately 800 can ends per minute while the can end 10 is rotated. The compound is applied to the seaming flange 13 acts as a sealant to prevent any leakage of the contents of the can through the mechanical joint.

The compound typically is a rubber-like sealant, the specific chemistry of which varies, depending upon the ultimate product introduced into the can, as is well known in the art.

The detector further includes an infrared sensor 20, a bifurcated fiber optic cable 22, a control panel 24 and a reject mechanism 26.

The infrared sensor 20 can be a Smarteye Model SDF 1 distributed by the TriTronics Company, Inc. of Tampa, Fla.

The bifurcated fiber optic cable 22 includes a first split segment 22a, a second split segment 22b and a common segment 22c. The first split segment 22a is coupled to an infrared output 20a of the sensor 20, and the second split segment 22b is coupled to an infrared input 20b of the sensor 20. The common segment 22c is coupled on a bracket (not shown) directed toward the seaming flange 13 to be monitored, the end of the common segment 22c being positioned a distance of approximatey ¼" to ⅜" therefrom. Separate transmitting and receiving fiber optic cables can be utilized rather than the bifurcated fiber optic cable 22 without departing from the scope of the invention.

The infrared sensor 20 generates an infrared signal at the infrared output 20a, which is transmitted via the first split segment 22a through the common segment 22c towards the seaming flange 13. The generated infrared signal is reflected by the seaming flange 13, and a portion thereof travels back, first via the common segment 22c then via the second split segment 22b, ultimately to be received by the infrared sensor 20 at the infrared input 20b. The magnitude of the reflected infrared signal depends upon the reflectivity of the seaming flange 13 where the generated infrared signal was reflected.

The infrared sensor 20 further generates an internal, adjustable reference signal and includes a comparator 27 for comparing the reference signal with the magnitude of the reflected infrared signal.

The can end 10 is typically made of aluminum or some other metal, and therefore it reflects a relatively large portion of the generated infrared signal. On the other hand, the compound reflects a much smaller portion of the generated infrared signal. Thus, the magnitude of the reflected infrared signal will be relatively high when no compound is present on the seaming flange 13, but will be relatively low when the compound is present in the seaming flange 13. Thus, the reference signal is set at a level representing the midpoint between the magnitude of the reflected infrared signal when the compound is not present and the magnitude of the reflected infrared signal when the compound is present. So long as the magnitude of the reflected infrared signal remains below the reference signal, indicating proper application of the compound, the comparator 27 remains off. However, when the magnitude of the reflected infrared signal is greater than the reference signal, indicating a lack of the compound, the comparator 27 turns on, generating a reject signal.

The reject signal is process by the control panel 24 to activate the reject mechanism 26 to reject the detected defective can end 10, as is well known in the art.

Because the can end 10 can be made of various materials having various finishes, its reflectivity can also vary widely. Further, because compounds of varying chemistries are utilized, depending upon the ultimate contents of the can, the compounds also can have varying degrees of reflectivity. Therefore, the reference signal can be manually adjusted to a proper level depending on the particular can end and compound utilized.

The diameter of the common segment 22c of the bifurcated fiber optic cable 22 is very small, and the fibers have a diameter of approximately 0.026", which is direceted to the center of the well 14a.

Because the fiber optic cable 22 carries both the generated and reflected infrared signals, and is flexible, it can be seen that according to the invention, the infrared sensor 20 can be placed distance from the can end 10 in whatever convenient location is available.

It will be understood that the invention may be embodied in other specific forms without departing from the spirit or central characteristics thereof. The present examples and embodiments, therefore, are to be considered in all respects as illustrative and not restrictive, and the invention is not to be limited to the details given herein.

I claim:

1. A detector for a can making apparatus applying a compound to a seaming flange of a can end, the detector for detecting the presence of said compound on said seaming flange of said can end comprising:

means for generating an infrared signal;

means for receiving an infrared signal;

a first fiber optic cable having a first end coupled to said infrared signal generating means and a second end directed toward said seaming flange of said can end, said first fiber optic cable for transmitting said generated infrared signal toward said seaming flange of said can end, causing said seaming flange to reflect a portion of said generated signal as a reflected signal, wherein said seaming flange reflects a first proportion of said generated infrared light in the absence of said compound and a second proportion of said generated infrared light in the presence of said compound;

a second fiber optic cable having a first end directed toward said seaming flange of said can end and a second end coupled to said infrared signal receiving means, said second fiber optic cable for transmitting said reflected infrared signal from said seaming flange to said infrared signal receiving means;

means for comparing said reflected infrared signal received by said infrared signal receiving means to a reference value representing a desired thickness of said compound applied to said seaming flange; and means for generating a reject signal in the event that said comparing means indicates that less than said desired thickness of said compound has been applied.

2. The detector of claim 1 wherein said reference value is adjustable.

3. The detector of claim 1 wherein said second end of said first fiber optic cable and said first end of said second fiber optic cable are a distance of the order of ¼" to ⅜" away from said seaming flange.

4. The detector of claim 1 including means for rejecting said can end in response to said reject signal.

5. The detector of claim 1 wherein said first and second fiber optic cables together comprise a bifurcated fiber optic cable, said bifurcated fiber optic cable having first and second split segments and a common segment, and said first split segment is coupled to said infrared generating means, said second split segment is coupled to said infrared receiving means, and said common segment is directed toward said seaming flange.

6. The detector of claim 5 wherein said common segment is a distance of the order of ¼" to ⅜" away from said seaming flange.

7. A detector for a can making apparatus applying a compound to a can end, the detector for detecting the presence of said compound on said can end comprising:
 means for generating an infrared signal;
 means for receiving an infrared signal;
 a first fiber optic cable having a first end coupled to said infrared signal generating means and a second end directed toward said can end, said first fiber optic cable for transmitting said generated infrared signal toward said can end, causing a portion of said generated signal to reflect as a reflected signal, wherein said can end reflects a first proportion of said generated infrared light in the absence of said compound and a second proportion of said generated infrared light in the presence of said compound, said second proportion being less than said first proportion;
 a second fiber optic cable having a first end directed toward said can end and a second end coupled to said infrared signal receiving means, said second fiber optic cable for transmitting said reflected infrared signal from said can end to said infrared signal receiving means;
 means for comparing said reflected infrared signal received by said infrared signal receiving means to a reference value representing a minimum thickness of said compound applied to said can end; and
 means for generating a reject signal in the event that said comparing means indicates that said reflected signal is greater than said reference value.

8. The detector of claim 7 wherein said reference value is adjustable.

9. The detector of claim 7 wherein said second end of said first fiber optic cable and said first end of said second fiber optic cable are positioned a distance of the order of $\frac{1}{4}''$ to $\frac{3}{8}''$ away from said can end.

10. The detector of claim 7 including means for rejecting said can end in response to said reject signal.

11. The detector of claim 7 wherein said first and second fiber optic cables together comprise a bifurcated fiber optic cable, said bifurcated fiber optic cable having first and second split segments and a common segment, and said first split segment is coupled to said infrared generating means, said second split segment is coupled to said infrared receiving means, and said common segment is directed toward said can end.

12. The detector of claim 11 wherein said common segment is positioned a distance of the order of $\frac{1}{4}''$ to $\frac{3}{8}''$ away from said can end.

13. A detector for a can making apparatus applying a compound to a seaming flange of a can end, the detector for detecting the presence of said compound on said seaming flange of said can end comprising:
 means for generating an infrared signal, said infrared signal generating means located distant from said seaming flange;
 means for receiving an infrared signal, said infrared signal generating means located distant from said seaming flange;
 a bifurcated fiber optic cable having first and second split segments and a common segment, and said first split segment coupled to said infrared generating means, said second split segment coupled to said infrared receiving means, and said common segment directed toward said seaming flange, said fiber optic cable for transmitting said generated infrared signal toward said seaming flange of said can end, causing said seaming flange to reflect a porton of said generated signal as a reflected signal, and transmitting said reflected signal to said receiving means, wherein said seaming flange reflects a first proportion of said generated infrared light in the absence of said compound and a second proportion of said generated infrared light in the presence of said compound;
 means for comparing said reflected infrared signal received by said infrared signal receiving means to a reference value representing a desired thickness of said compound applied to said seaming flange; and
 means for generating a reject signal in the event that said comparing means indicates that less than said desired thickness of said compound has been applied.

* * * * *